United States Patent
Dupré et al.

[11] 4,051,145
[45] Sept. 27, 1977

[54] FLUORINATED INDAZOLE DERIVATIVES AND A PROCESS FOR THEIR PREPARATION

[75] Inventors: Victor Marie Dupré, Louvres; Jacques Pierre Edmond Pechmeze, Paris; Robert Frédéric Michel Sureau, Enghien les Bains, France

[73] Assignee: Produits Chimiques Ugine Kuhlmann, Paris, France

[21] Appl. No.: 562,062

[22] Filed: Mar. 26, 1975

[30] Foreign Application Priority Data

Mar. 29, 1974 France ............... 74.11262

[51] Int. Cl.$^2$ .......................... C07D 231/56
[52] U.S. Cl. ................................ 548/372
[58] Field of Search ....................... 260/310 C

[56] References Cited

U.S. PATENT DOCUMENTS

| 3,133,081 | 5/1964 | Lafferty et al. | 260/310 C |
| 3,736,332 | 5/1973 | Butula | 260/310 R |

FOREIGN PATENT DOCUMENTS

| 2,257,080 | 5/1973 | Germany |

OTHER PUBLICATIONS

Chem. Ber. 106 pp. 2870–2876 (1973).
Chem. Abstracts 52: 12849f.

*Primary Examiner*—Donald B. Moyer
*Attorney, Agent, or Firm*—Beveridge, DeGrandi, Kline, Lunsford

[57] ABSTRACT

Compound of the formula:

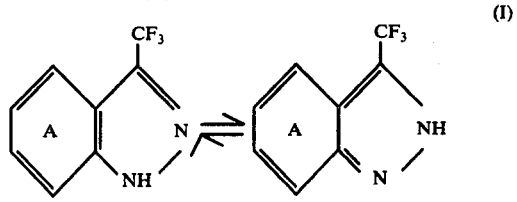

(I)

in which the nucleus A is unsubstituted or substituted by one or two nitro, amino, alkyl, alkoxy, chlorine or bromine and the alkyl and alkoxy each contain up to two carbon atoms and process for the preparation of such compounds which comprises diazotizing an aniline of the formula:

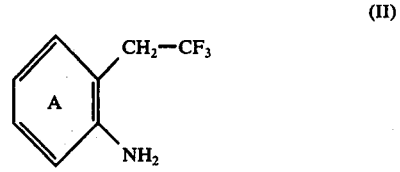

(II)

in which the nucleus A is unsubstituted or substituted by one or two nitro, amino, alkyl, alkoxy, chlorine or bromine, the alkyl and alkoxy each containing up to two carbon atoms and cyclizing the diazo derivative obtained.

6 Claims, No Drawings

FLUORINATED INDAZOLE DERIVATIVES AND A PROCESS FOR THEIR PREPARATION

The present invention concerns fluorinated indazole derivatives and a process for their preparation. These derivatives are new compounds which may be used, for example, as intermediate products for the preparation of dyestuffs or pharmaceutical products, and they may also be used as phytopharmaceutical products.

According to the present invention fluorinated indazole derivatives are provided having the general formula:

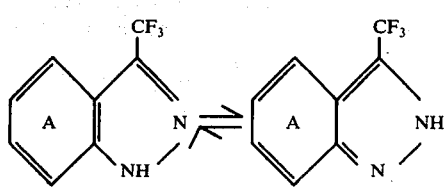

in which the nucleus A may be substituted by one or two nitro, amino, alkyl or alkoxy groups or chlorine or bromine atom and the alkyl and alkoxy groups each contain up to two carbon atoms.

They may be prepared for example in a simple way by diazotising 2-(2,2,2-trifluroroethyl)-anilines of the formula:

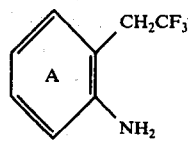

in which the nucleus A may be substituted as indicated above any cyclising the diazo derivative obtained.

The diazotisation may be effected by a method known per se, for example, by means of a salt of nitrous acid, in aqueous solution in the presence of dilute mineral acid. The cyclisation to an indazole derivative may then be effected, for example, by heating the solution of the diazo derivative, previously buffered, for example, by an alkali metal acetate or phosphate.

The diazotisation may also be effected for example in glacial acetic acid medium at ambient temperature, by the addition of a concentrated aqueous solution of an alkali metal nitrite. The cyclisation then takes place of itself in a variable period of time which may be from some hours to three days.

Nirtrated or halogenated derivatives of formula I, may be obtained by nitration or halogenation of the 3-trifluoromethylindazole previously synthesised.

The 2-(2,2,2-trifluoro-ethyl)-anilines of formula (II) are themselves new products and are claimed in patent application Ser. No. 562,063 filed today in the names of Foulletier, Pechmeze and Sureau claiming priority of French Patent Application No. 74 11263. The compounds falling within formula (I) are found to be particularly interesting as selective herbicides. This selectivity is manifested with respect to the Gramineae and Cucurbitaceae among others. The treatment is preferably applied after starting up by means of aqueous dispersions at doses of 1 to 2 kg per hectare.

The invention is illustrated by the following Examples in which the parts are parts by weight unless the contrary is indicated.

EXAMPLE 1

18.9 parts of 2-(2,2,2-trifluoro-ethyl)-aniline are dissoved in 700 parts by volume of glacial acetic acid. 14 parts by volume of a 50% aqueous solution of sodium nitrite are poured at one go into this well stirred solution. The temperature of the mass rises from 20° C. 27° C. The stirring is maintained at ambient temperature for about 15 hours, after which the intermediate diazo derivative has totally disappeared. A large part of the acetic acid is eliminated by distillation in vacuum so as to give a volume of about 100 parts. Then the solution is run into 160 parts of cold water with stirring. The precipitate of 3-trifluoromethyl-indazole formed is filtered off and washed with water: crude M.p. 98° C. It is recrystallised from boiling water for analysis. White needles of M.p. 104° C. (Kofler stage) are obtained; dry weight after recrystallisation 11.4 parts.

| Analysis for $C_8H_5N_2F_3$: | | | | | | | | | |
|---|---|---|---|---|---|---|---|---|---|
| Calculated: | 0% | 51.6 | H% | 2.69 | N% | 15.05 | F% | 30.6 |
| Found: | | 51.6 | | 2.88 | | 15.1 | | 30.3 |
| | | 51.7 | | 2.98 | | 15.2 | | 30.6 | the 2-(2,2,2-trifluoro-ethyl)-aniline is obtained in the following way:

465 parts of aniline and 237 parts of 1-chloro-2,2,2-trifluoro-ethane are heated for 6 hours at 250°–255° C. in an autoclave of stainless steel. After cooling, the contents of the autoclave are poured into 1000 parts by volume of 2N sulphuric acid, and the distinctly acid mixture is steam distilled. The distillate leaves a deposit of an organic layer which is dissolved in 500 parts by volume of benzene. This benzene solution is extracted 4 times with 100 parts each of N hydrochloric acid. The aqueous phase, made alkaline with a solution of caustic soda, is again extracted with benzene. After drying and evaporation of the benzene, 62 parts of a white solid are obtained which, after recrystallisation from hexane, melts at 49° C. The IR and NMR spectra confirm that it is 2-(2,2,2-trifluoro-ethyl)-aniline.

EXAMPLE 2

11 parts of 4-nitro-2-(2,2,2-trifluoro-ethyl)-aniline are dissolved in 350 parts by volume of glacial acetic acid. To this solution at 15° C. are added all at once, with stirring 7 parts by volume of a 50% solution of sodium nitrite. Stirring is effected for 3 hours at ambient temperature, then the product is allowed to stand until the diazo derivative has disappeared. The acetic acid is evaporated under reduced pressure practically to dryness and the residue is taken up in 28 parts of water. The solid is filtered off, washed and dried. After recrystallisation in a 1/1 mixture of methanol and water, 7.4 parts of 3-trifluoromethyl-5-nirtro-indazole are obtained. M.p. 167° C.

| Analysis for $C_8H_4F_3N_3O_2$ | | | | | | | | | |
|---|---|---|---|---|---|---|---|---|---|
| Calculated: | C% | 41.56 | H% | 1.73 | N% | 18.18 | F% | 24.68 |
| Found: | | 41.7 | | 1.92 | | 17.7 | | 24.3 |

The NMR spectrum confirms that it is really the product nitrated at position 5 and free from isomer.

The 4-nitro-2-(2,2,2-trifluoro-ethyl)-aniline is prepared as follows:

35 parts of 2-(2,2,2-trifluoro-ethyl)-aniline are dissolved in 100 parts by volume of glacial acetic acid. 40 parts of acetic anhydride are added and the mixture is heated for 2 hours at 110° C. The product which crystallises heavily on cooling is filtered off, washed and dried. 34 parts of 2-(2, 2,2-trifluoro-ethyl)-acetanilide of M.p. 187° C. are obtained. 32.6 parts of the acetyl derivative are gradually introduced, so as not to exceed the temperature of 0° C. into 90 parts by volume of 66° Be sulphuric acid. 6.5 parts of nitric acid (d1.52) are added while stirring without exceeding a temperature of 0° C., stirring is carried on for 1 hour at this temperature, then for 2 hours while allowing the temperature to rise to about 20° C. The mixture is poured on 500 parts of crushed ice. The precipitate is filtered off, washed until the washings are neutral and dried. 37 parts of 4-nitro-2-(2,2,2-trifluoro-ethyl)-acetanilide are obtained which is recrystallised in acetic acid for the analysis. M.p. 238° C. The NMR spectrum confirms that it is the derivative nitrated at position 4 free from isomer. 53 parts of this nitro derivative are heated under relux in a mixture of 300 parts by volume of 2N hydrochloric acid and 150 parts by volume of ethanol until complete solution is obtained. The solution is cooled and made alkaline by the addition of aqueous caustic soda, then extracted with ether. After evaporation, 43.8 parts of 4-nitro-2-(2,2,2-trifluoro-ethyl) -aniline are obtained which, recrystallised from toluene, melts at 101° C.

EXAMPLE 3

18.6 parts of 3-trifluoromethyl-indazole described in Example 1 are introduced, without exceeding a temperature of 5° C. into 30 parts by volume of 66° Be sulphuric acid. 20 parts of sulphonitric acid containing 33% of HNO$_3$ are gradually introduced into the solution obtained, with stirring and without exceeding 5° C. The solution is then stirred again for 1 hour at 5° C. then poured into 200 parts of a 1/1 mixture of crushed ice and water. The solid is filtered off, washed until the washings are neutral and dried. After recrystallisation a product is obtained which melts at 160° C. The NMR spectrum shows that it is a mixture containing 86% of 5-nitro derivative identical to that described in Example 2, accompanied by 14% of 3-trifluoro-methyl-7-nitro-indazole.

| Analysis for C$_8$H$_4$F$_3$N$_3$O$_2$ | | | | | | | | | |
|---|---|---|---|---|---|---|---|---|---|
| Calculated: | C% | 41.56 | H% | 1.73 | N% | 18.18 | F% | 24.68 |
| Found: | | 41.6 | | 1.61 | | 18.4 | | 25.2 |

EXAMPLE 4

A solution of 23.1 parts of 2-trifluoro-methyl-5-nirtro-indazole in 150 parts of methanol is subjected to catalytic reduction with hydrogen in the presence of a catalyst based on palladium. The reduction is effected at ordinary temperature. When the hydrogen is no longer absorbed, the alcohol is driven off and the solid residue is recrystallised from water. 3-trifluoro-methyl-5-amino-indazole of M.p. 152° C. is thus obtained.

| Analysis for C$_8$H$_6$N$_3$F$_3$ | | | | | | | | | |
|---|---|---|---|---|---|---|---|---|---|
| Calculated: | C% | 47.76 | H% | 2.98 | N% | 20.88 | F% | 28.38 |
| Found: | | 47.6 | | 2.85 | | 20.9 | | 27.9 |
| -continued |||||||||
| Analysis for C$_8$H$_6$N$_3$F$_3$ | | | | | | | | |
| | 47.7 | | 3.14 | | 20.9 | | 28.3 | |

EXAMPLE 5

18 parts of 2-(2,2,2-trifluoro-ethyl)-4-bromo-aniline are dissolved in 490 parts by volume of glacial acetic acid. To this solution, well stirred at 15° C., is added all at once a solution of 4.9 parts of sodium nitrite in 11.9 parts of water. At the end of 3 days, the acetic acid is evaporated and the residue is taken up in 40 parts of water, the solid filtered off, washed and dried. 18 parts of 3-trifluoromethyl-5-bromo-indazole are thus obtained.

The product is recrystallised in 80 parts of water and 20 parts of ethanol. M.P. 168°–169° C.

| Analysis for C$_8$H$_4$Br F$_3$N | | | | | | |
|---|---|---|---|---|---|---|
| Calculated: | C% | 36.23 | H% | 1.51 | N% | 10.56 |
| Found: | | 37.0 | | 1.75 | | 10.8 |

The 2-(2,2,2-trifluoro-ethyl)-4-bromo-aniline is prepared in the following way:

A mixture comprising 21.7 parts of 2-(2,2,2-trifluoro-ethyl)-acetanilide, 9 parts of anhydrous sodium acetate, 200 parts of glacial acetic acid and 16 parts of bromine is stirred for 2 hours at the ambient temperature, then at 40° C. for 15 minutes, and finally for 1 hour at 60° C. After cooling the solution is run into 500 parts of water. It is filtered and the precipitate of 2-trifluoroethyl-4-bromo-acetanilide obtained is washed and dried, say 23 parts of M.p. 216° C. This product is taken up at the boil for 6 hours in 200 parts of 2N hydrochloric acid and 100 parts of ethanol. After cooling, the mixture is made alkaline by the addition of 70 parts by volume of 30% soda lye and the precipitate is extracted with ether. After evaporation of the solvent, 19 parts of 2-(2,2,2-trifluoro-ethyl)-4-bromo-aniline are obtained, which are recrystallised from hexane, M.p. 100°–101° C.

EXAMPLE 6

4.7 parts of 3-trifluoromethyl-indazole are dissolved in 10 parts by volume of dimethylformamide, then 4 parts of bromine are gradually added to this solution, well stirred at ambient temperature. The temperature reached 45° C. The stirring is maintained for 3 hours, then the mixture is run on 200 parts of ice water. An oil separates which gradually crystallises. The crystals are filtered off, washed copiously and dried in vacuo.

The product is recrystallised in ligroin b.p. 70°–100° C. A product melting at 164° C. is obtained. It contains, according to gas-liquid chromatography, 91.2% of 3-trifluoro-methyl-5-bromo-indazole identical with the compound described in Example 5, and 8.6% of the 7-bromo isomer.

EXAMPLE 7

On operating as in Example 6, but replacing the bromine by an equivalent amount of chlorine, there is obtained after an identical treatment a chlorinated compound made up of 92.9% of 5-chloro-3-trifluoromethyl-indazole, 2.2% of the 7-chloro isomer and 4.7% of initial 3-trifluoromethyl-indazole. M.p. 164° C.

| Analysis for $C_8H_4ClF_3N$ | | | | | | |
|---|---|---|---|---|---|---|
| Calculated: | C% | 43.55 | H% | 1.83 | N% | 12.7 |
| Found: | | 43.65 | | 1.69 | | 12.95 |

We claim:

1. Compound of the formula:

(I)

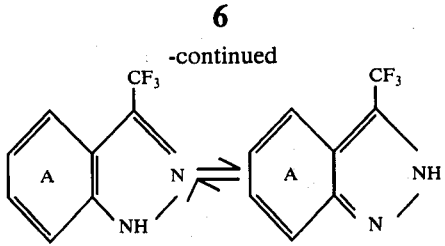

in which the nucleus A is unsubstituted or substituted by one or two nitro, amino, alkyl, alkoxy, chlorine or bromine and the alkyl and alkoxy each contain up to two carbon atoms.

2. The compound 3-trifluoromethyl-5-nitro indazole.
3. The compound 3-trifluoromethyl-5-amino-indazole.
4. The compound 3-trifluoromethyl-indazole.
5. The compound 3-trifluoromethyl-5-bromo-indazole.
6. The compound 3-trifluoromethyl-5-chloro-indazole.

* * * * *